United States Patent
Kaigler, Sr.

(10) Patent No.: US 8,142,194 B2
(45) Date of Patent: Mar. 27, 2012

(54) IMPLANTS AND METHODS FOR PERFORMING GUMS AND BONE AUGMENTATION AND PRESERVATION

(75) Inventor: Darnell Kaigler, Sr., Detroit, MI (US)

(73) Assignee: Innovative Health Technologies, LLC, Anchorage, AK (US)

( * ) Notice: Subject to any disclaimer, the term of this patent is extended or adjusted under 35 U.S.C. 154(b) by 50 days.

(21) Appl. No.: 12/619,546

(22) Filed: Nov. 16, 2009

(65) Prior Publication Data

US 2011/0117520 A1    May 19, 2011

(51) Int. Cl.
*A61C 13/00* (2006.01)
*A61K 6/00* (2006.01)

(52) U.S. Cl. .................. 433/226; 433/212.1; 433/228.1; 523/116

(58) Field of Classification Search .................. 433/226, 433/212.1, 228.1; 523/116
See application file for complete search history.

(56) References Cited

U.S. PATENT DOCUMENTS

| | | | |
|---|---|---|---|
| 5,085,861 A | 2/1992 | Gerhart et al. | |
| 5,542,973 A | 8/1996 | Chow et al. | |
| 6,213,774 B1 | 4/2001 | Lazarof | |
| 6,376,573 B1 * | 4/2002 | White et al. | 523/115 |
| 6,593,394 B1 | 7/2003 | Li et al. | |
| 7,811,291 B2 * | 10/2010 | Liu et al. | 606/94 |
| 2005/0081750 A1 * | 4/2005 | Xu et al. | 106/35 |
| 2005/0209704 A1 * | 9/2005 | Maspero et al. | 623/23.5 |
| 2005/0256222 A1 * | 11/2005 | Jones et al. | 523/116 |
| 2009/0028960 A1 * | 1/2009 | Leonard et al. | 424/602 |
| 2009/0131945 A1 | 5/2009 | Liu et al. | |
| 2011/0097420 A1 * | 4/2011 | Lin et al. | 424/501 |

* cited by examiner

*Primary Examiner* — Tae H Yoon
(74) *Attorney, Agent, or Firm* — Dickstein Shapiro LLP

(57) ABSTRACT

Embodiments described herein are related to fillers that are placed within an extraction site in need of bone augmentation and preservation. The fillers encourage sufficient new bone growth in order that normal jaw bone deterioration following tooth removal is prevented. The fillers create, arrange, and assemble an ideal growth environment for new bone growth to rapidly grow and preserve the original contours of an individual's jaw bone. Further embodiments described herein are related to dental implants that are arranged to provide a scaffold upon which a damaged or missing dental papilla may regrow. The dental implants may include a micro-pattern to facilitate directional cell growth.

11 Claims, 10 Drawing Sheets

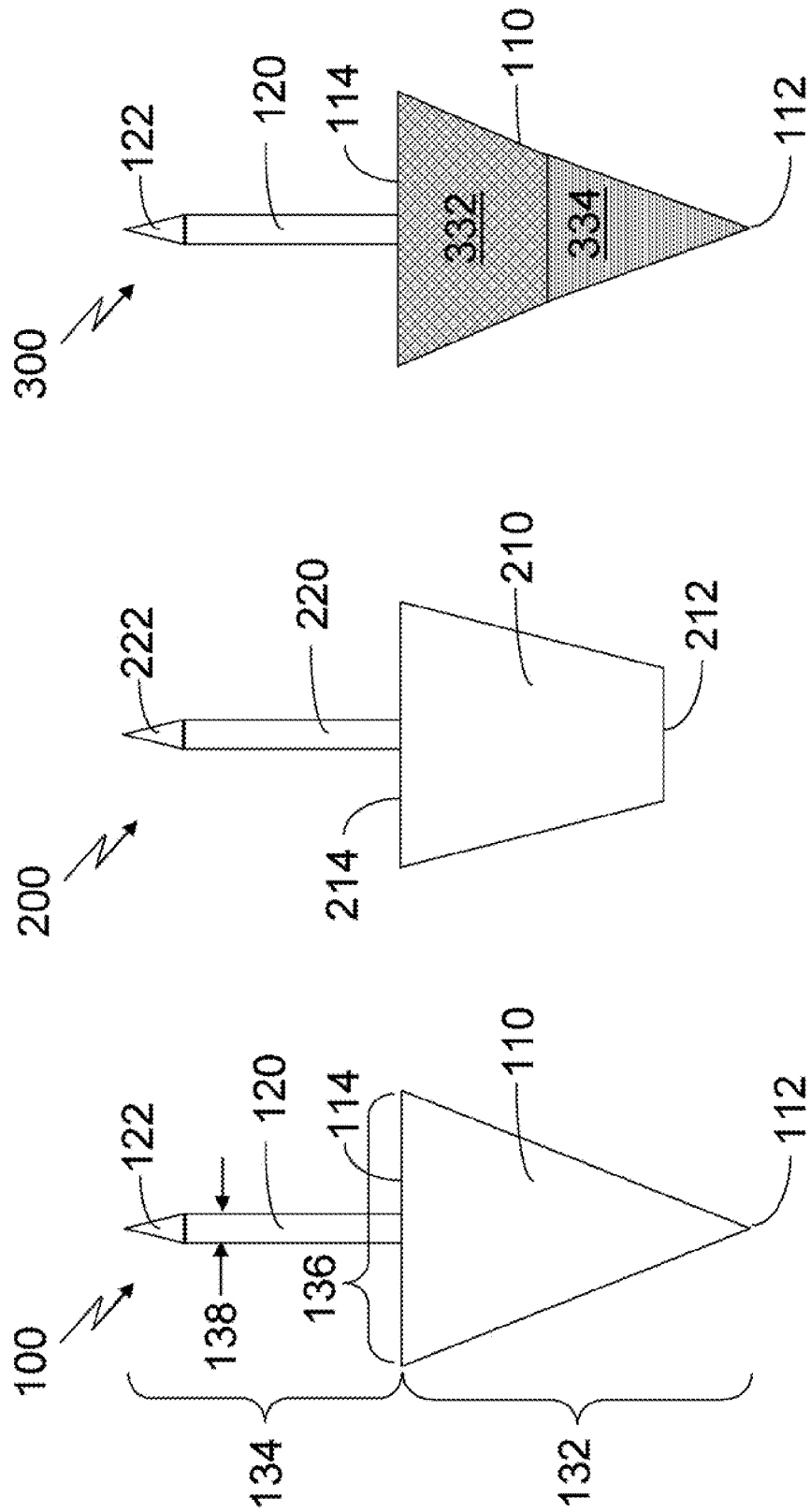

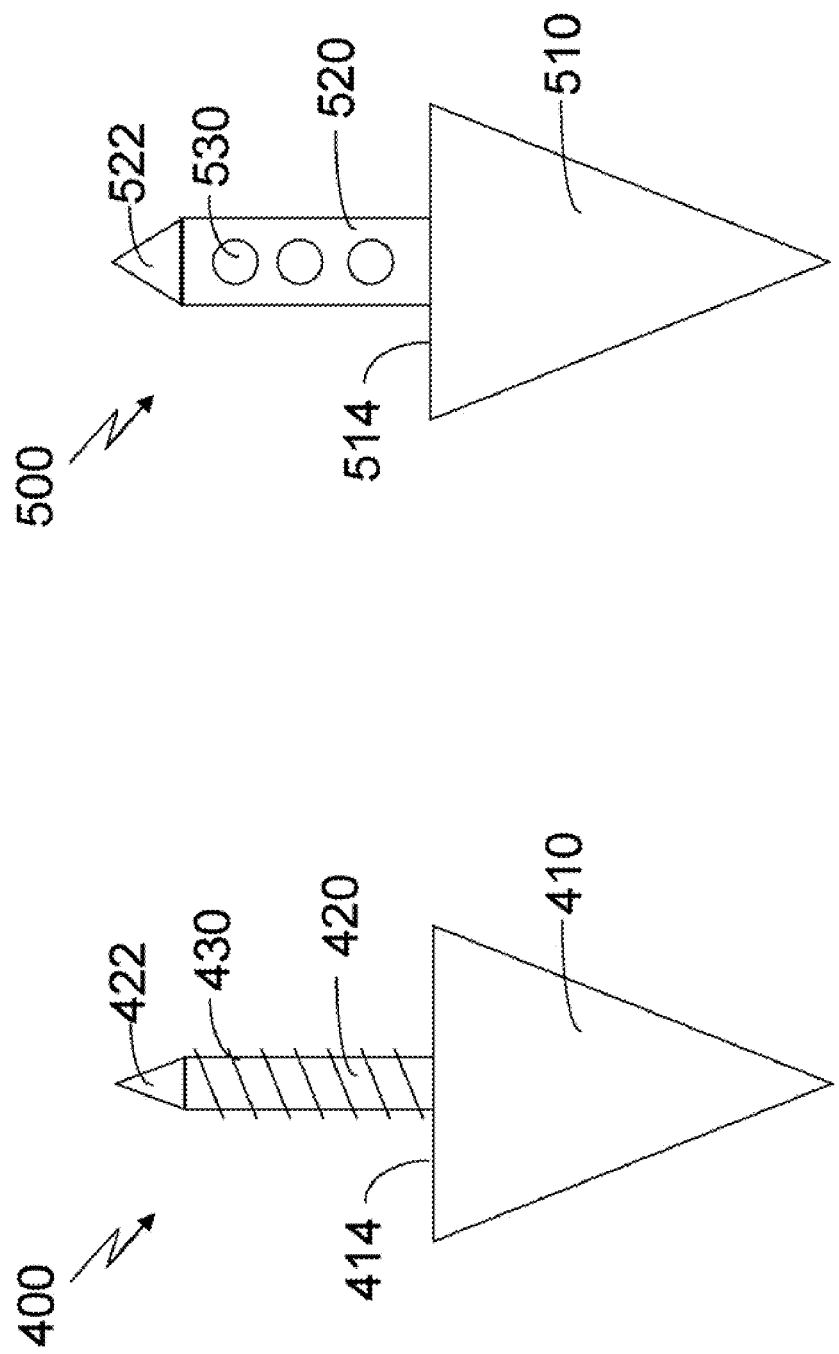

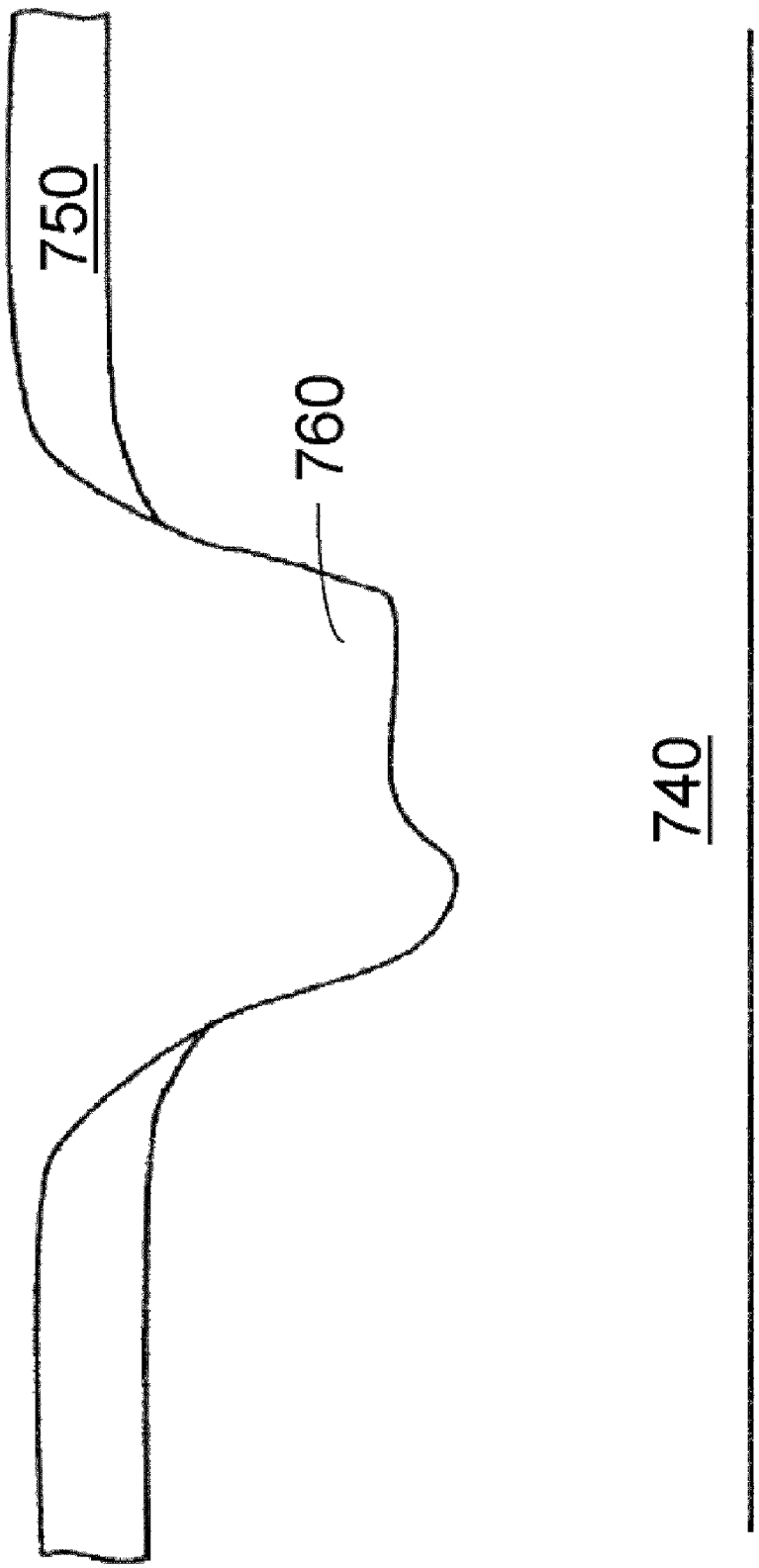

IMPLANTS AND METHODS FOR PERFORMING GUMS AND BONE AUGMENTATION AND PRESERVATION

FIELD

Embodiments described herein relate generally to apparatuses and methods for dental surgery, and particularly to apparatuses and methods for performing gingival (gum) and bone preservation and/or augmentation.

BACKGROUND

When an extracted or otherwise missing tooth is not immediately grafted or replaced with an implant, atrophy of the jaw (alveolar) bone occurs over time. Consequently, individuals who have been partially edentulous for an extended period of time are left with an atrophic alveolar ridge that cannot securely support a denture. Furthermore, the edentulous individual faces deteriorated esthetics and a compromised ability to chew and must be rehabilitated leaving the quality of the individual's oral health in an unfortunate state.

The inner portions of the alveolar bone are composed of soft trabecular bone which has the unique characteristic of being capable of absorbing the shocks caused by the movement of teeth during speech, eating, etc. The removal of a tooth and the resulting absence of the bone pressure stimuli in the area causes the alveolar bone to resorb in that area. The result can be loss of 40-60% of the alveolar ridge's former height. After this initial 40-60% loss, the alveolar bone can continue to resorb at a bone loss rate of 0.5-1.0 mm per year.

In addition, when teeth are extracted, the lack of supporting bone fails to sufficiently support the load of a later inserted prosthesis or implant. This is a byproduct of the alveolar bone becoming weaker due to the lack of internal stimulation leading to a softer, porous, less dense, and spongier nature of the deteriorated bone. In addition, dental implants are prone to fail due to the porous nature of the bone and a lack of bone density.

In healthy teeth and gingiva (gums), small spaces (embrasures) may exist between teeth near the papilla of the gum line. The dental papillae are small triangular portions of the gum line that cover the spaces between the teeth. In certain cases, the papilla may become damaged due to improper oral hygiene or gum diseases, such as gingivitis and periodontitis. Recession of the gums causes the embrasure spaces to increase in size. In severe cases, known as "black triangle disease," the spaces may expand and become large voids between the teeth. The diastemas can be unsightly and, in severe cases, may cause difficulty in speaking and/or eating. Black triangle disease has been treated by various methods including gum grafts and other surgeries. However, because the gums have no substrate on which to form, regeneration of the papilla may be slow or impossible.

Improved materials and techniques for augmenting, preserving and supporting gum and bone growth are needed to re-grow missing or damaged gum tissue, decrease alveolar ridge deterioration and enhance the alveolar bone support of an oral prosthesis or implant.

BRIEF SUMMARY

Embodiments described herein include a dental implant that provides a substrate on which receded gum tissue of the papilla may regrow. The dental implant includes a body and an anchor attached to the body. The anchor is inserted into the jawbone of a patient to anchor the dental implant in the area of the papilla. The body may include micro-textures that facilitate uni- or bi-directional cellular growth to facilitate regrowth of the gums at the gum line. The dental implant may be made completely or partially out of biodegradable material so that the dental implant need not be removed from the patient's jaw bone.

Further embodiments described herein include a filler that is either placed within a fresh extraction site of the gum or onlayed on existing bone tissue in a viscous form to conform to the extraction site. The filler is designed to facilitate bone formation (preservation or augmentation) within the tooth socket. The filler can be used to fill the various sizes and shapes of the jaw bone deficiency to which it conforms. The filler comprises one or more biocompatible materials. The one or more biocompatible materials are injected and solidified into a solid, matrix, or mesh-like structure designed to enhance a bone growth environment by osteoinduction or osteoconduction. Optionally, a reinforced polymer and/or composite coating may be subsequently injected to cover and protect the filler from the oral environment. After insertion and solidification, the filler facilitates new bone growth for preservation and/or augmentation. Over time, an integrated bone tissue, which is the obtained integration between the growing bone and the filler, develops. Once adequate bone growth has occurred, the integrated bone structure can support a prosthesis or can be used as an area to accommodate a dental implant device. Thus, the resulting foundation can provide enhanced support, fixation, and anchoring strength for a prosthesis or implant device due to the preservation and/or augmentation of the bone tissue.

BRIEF DESCRIPTION OF THE DRAWINGS

FIG. 1 illustrates a dental implant in accordance with an embodiment described herein.

FIG. 2 illustrates a dental implant in accordance with another embodiment described herein.

FIG. 3 illustrates a dental implant in accordance with another embodiment described herein.

FIG. 4 illustrates a dental implant in accordance with another embodiment described herein.

FIG. 5 illustrates a dental implant in accordance with another embodiment described herein.

FIGS. 7A-7C illustrate various stages of performing bone augmentation in accordance with an embodiment discussed herein.

DETAILED DESCRIPTION

Figure 6A:
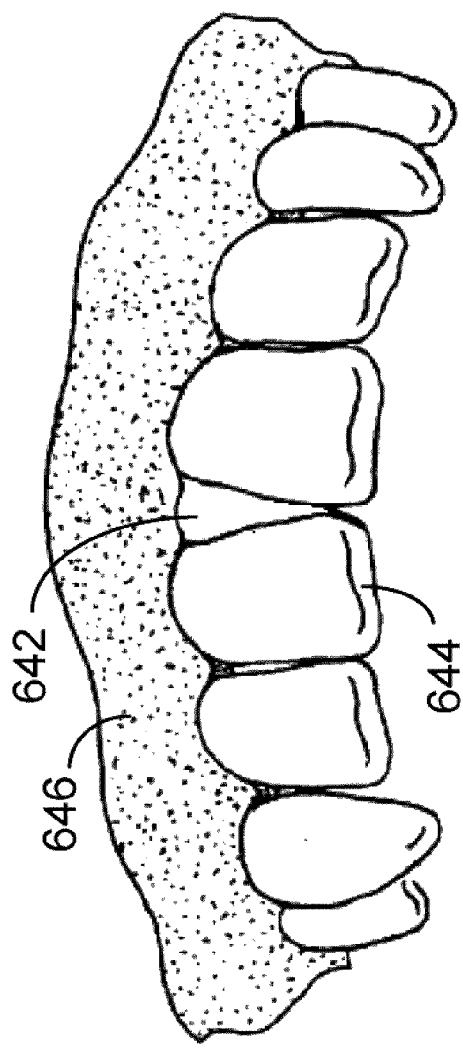
FIGS. 6A-6C illustrate various stages of a method of implanting a dental implant in accordance with an embodiment discussed herein.

Embodiments discussed herein provide apparatus and methods for preserving and augmenting bone growth particularly well suited for decreasing alveolar ridge deterioration, enhancing support of a prosthesis, and regrowing gum tissue at the gum line in the area of the dental papilla. In the following description, numerous specific details are set forth, such as material types, dimensions, specific tissues, etc., in order to provide a thorough understanding of the present embodiments. Practitioners having ordinary skill in the biomedical arts will understand that the various embodiments described herein may be practiced without many of these details. In other instances, well-known devices, methods, and biochemical processes have not been described in detail to avoid obscuring the claimed embodiments.

As described above, in a phenomenon known as "black triangle disease," the portion of the gum line known as the papilla may become damaged leaving large spaces between the teeth. Because the gums have no substrate or other support upon which to regrow, regeneration of the papilla may be slow or impossible. Embodiments discussed herein offer solutions to this problem by providing a dental implant that provides a substrate on which the papilla may regrow.

Turning now to FIG. 1, where like elements are designated by like numerals, there is shown a dental implant 100 having a body 110 and an anchor 120 attached to the body 110. The anchor 120 is designed to be implanted into the jawbone of a patent to secure the body 110 partially within the gums and further extended out of the gums into the area in which an otherwise undamaged papilla would be located. The body 110 includes a base 114 having a width 136 and a terminal end 112. The body has a height 132 and a width 136 appropriately sized to be located partially within the gums while extending out of the gums to occupy the area otherwise occupied by the papilla. The height 132 and width 136 of the body may be modified to fit more precisely in a particular interdental space.

The anchor 120 is attached to the body 110 and protrudes from the base 114 of the body 110. The anchor 120 is designed to be implanted within the jaw bone of a patient to hold the dental implant 100 firmly in place. The anchor 120 includes a terminal end 122, which may be pointed for easier insertion into the jaw. The width 138 and length 134 of the anchor 120 may be modified to more precisely fit a patient's jaw and to hold the body 110 in an appropriate position. The anchor 120 may be made of materials such as metal, for example, surgical steel, ceramics, or polymers. The anchor 120 may be made of the same or different material than the body 110 and may be integral to the body 110. The anchor may be made up of a biomaterial so that it will be reabsorbed by the jaw.

The body 110 has a triangular shape in the embodiment shown in FIG. 1, however, other shapes are also possible, including rectangles, partial ovals, other polyhedrons, irregular shapes, and compound shapes. For example, FIG. 2 shows a dental implant 200 according to another embodiment including a body 210 having a base 214 and a terminal end 212, and an anchor 220 having a terminal end 222 and extending from the base 214 of the body 210. As shown in FIG. 2, the body 210 is shaped as a trapezoid.

The body 110 may be formed of a degradable material that allows the body 110 to remain intact for up to six months or more. The body 110 may be formed of a degradable or non-degradable bioceramic material, e.g., hydroxyapatite, reinforced polyethylene composite, betatricalciumphosphate, substituted calcium phosphates, bioactive glass, resorbable calcium phosphate, alumina, zirconia, etc. A composite material made up of a biodegradable polymer in combination with the bioceramic material may also be used to form the body 110. It should be appreciated that the body 110 may include any type of material known in the art having characteristics that result in non-toxic byproducts.

For example, the body 110 can be formed of synthetic polymers (alone or in combination) such as polyurethanes, polyorthoesters, polyvinyl alcohol, polyamides, polycarbonates, poly(ethylene)glycol, polylactic acid, polyglycolic acid, polycaprolactone, polyvinyl pyrrolidone, marine adhesive proteins, and cyanoacrylates, or analogs, mixtures, combinations, and derivatives of the above. The body 110 can also be formed of naturally occurring polymers or natively derived polymers (alone or in combination) such as agarose, alginate, fibrin, fibrinogen, fibronectin, collagen, gelatin, hyaluronic acid, and other suitable polymers and biopolymers, or analogs, mixtures, combinations, and derivatives of the above. Also, the body 110 can be formed from a mixture of naturally occurring biopolymers and synthetic polymers. Alternatively, the body 110 can be formed of a collagen gel, a polyvinyl alcohol sponge, a poly(D,L-lactide-co-glycolide) fiber matrix, a polyglactin fiber, a calcium alginate gel, a polyglycolic acid mesh, polyester (e.g., poly-(L-lactic acid) or a polyanhydride), a polysaccharide (e.g., alginate), polyphosphazene, or polyacrylate, or a polyethylene oxide-polypropylene glycol block copolymer. The body 110 can be produced from proteins (e.g. extracellular matrix proteins such as fibrin, collagen, and fibronectin), polymers (e.g., polyvinylpyrrolidone), or hyaluronic acid. Synthetic polymers can also be used, including bioerodible polymers, (e.g., poly(lactide), poly(glycolic acid), poly(lactide-co-glycolide), poly (caprolactone), polycarbonates, polyamides, polyanhydrides, polyamino acids, polyortho esters, polyacetals, polycyanoacrylates), degradable polyurethanes, non-erodible polymers (e.g., polyacrylates, ethylene-vinyl acetate polymers and other acyl substituted cellulose acetates and derivatives thereof), non-erodible polyurethanes, polystyrenes, polyvinyl chloride, polyvinyl fluoride, poly(vinylimidazole), chlorosulphonated polyolifins, polyethylene oxide, polyvinyl alcohol, Teflon®, and nylon. In other embodiments, the body 110 can be formed of a calcium phosphate ceramic, such as Tetracalcium Phosphate ($Ca_4P_2O_9$), Amorphous calcium Phosphate, alpha-Tricalcium Phosphate ($Ca_{10}(PO_4)2$), beta-Tricalcium Phosphate ($Ca_3(PO_4)2$), and Hydroxyapatite ($Ca_{10}(PO_4)_6(OH)_2$). In still other embodiments, the body 110 can be formed of Alumina or Zirconia.

The body 110 may include a coating to facilitate directional growth of the gum line along the dental implant 100 to facilitate faster healing. The polymer coating may be applied to the front and/or back of the body 110. In one embodiment, the coating is made up of a material having a thickness that allows the coating to remain intact for up to twenty-one days or more. The coating may be, for example, a polymer coating. The polymer coating may include various combinations of features such as biocompatibility and biodegradability, mechanical compliance with the gums, elicitation of a minimal inflammatory response, and the ability to deliver therapeutic or pharmaceutical drug formulations. The polymer coating may include a polyactic acid or other hydrogel. It should be appreciated that polymer coating does not have to be a complete polymer material, e.g., 100% polymer, but can be a composite material comprising a combination of any known bioceramic materials, composite hydrogels, and polymers. Moreover, the polymer coating can be made from a membrane such as collagen felt, or a similarly semi-rigid material, such as polylatic acid, polyether, etc. In the preferred embodiment, polymer coating is a bio-resorbable polymer. The preferred bio-resorbable polymer exhibits characteristics such as favorable handling properties that make the polymer easy to use (i.e., requires no additional training for the operator to learn how to use, long-term, indefinite shelf life, economical, does not add considerable cost to patients, conforms to the receptor site, highly biocompatible and partially biodegradable, low cost to manufacturer, biomimetic after placement, easy to distribute, supports cell growth and differentiation, and has chemotaxic properties (recruits wound healing host cells from surrounding tissue). The polymer may be infused within the filler as a liquid or viscous gel substance.

In one embodiment, the polymer coating may include a biodegradable condensation polymer of glycerol and a diacid, such as those described in U.S. Patent Application Publication No. 2003/0118692, the disclosure of which is hereby incorporated by reference in its entirety. For example, the polymer may be made up of poly(glycerol sebacate), poly(glycerol sebacate)-acrylate having low acrylation, poly(glycerol sebacate)-acrylate having high acrylation, poly(glycerol sebacate)-acrylate-co-poly(ethylene glycol) networks, poly(glycerol malonate), poly(glycerol succinate), poly(glycerol glutarate), poly(glycerol adipate), poly(glycerol pimelate), poly(glycerol suberate), poly(glycerol azelate), polymers of glycerol and diacids having more than 10, more than 15, more than 20, and more than 25 carbon atoms, polymers of glycerol and non-aliphatic diacids, and mixtures thereof. In various embodiments, amines and aromatic groups, such as terephthalic acid and carboxyphenoxypropane may be incorporated into the carbon chain. The diacids may also include substituents as well, such as amine and hydroxyl, to increase the number of sites available for cross-linking, amino acids and other biomolecules to modify the biological properties of the polymer, and aromatic groups, aliphatic groups, and halogen atoms to modify the inter-chain interactions within the polymer.

The polymer coating may further include a biomolecule, a hydrophilic group, a hydrophobic group, a non-protein organic group, an acid, a small molecule, a bioactive agent, a controlled-release therapeutic agent or pharmaceutical drug, or a combination thereof. The polymer may be seeded with cells compatible with the gum tissue to facilitate more rapid healing.

The polymer coating may include a micro-pattern arranged on its surface to increase its adhesion properties or to promote directional cell growth as described in U.S. Provisional Patent Application No. 61/238,019, which is hereby incorporated by reference in its entirety. The micro-pattern is sized to allow cells of the gums to grow directionally in one or two directions within the micro-pattern to promote rapid and efficient healing. In various embodiments, the micro-pattern may be formed of micro-tubes, micro-ridges, micro-troughs, or combinations thereof. In certain embodiments, the micro-pattern may be arranged directly onto the body of the dental implant.

Figure 10:
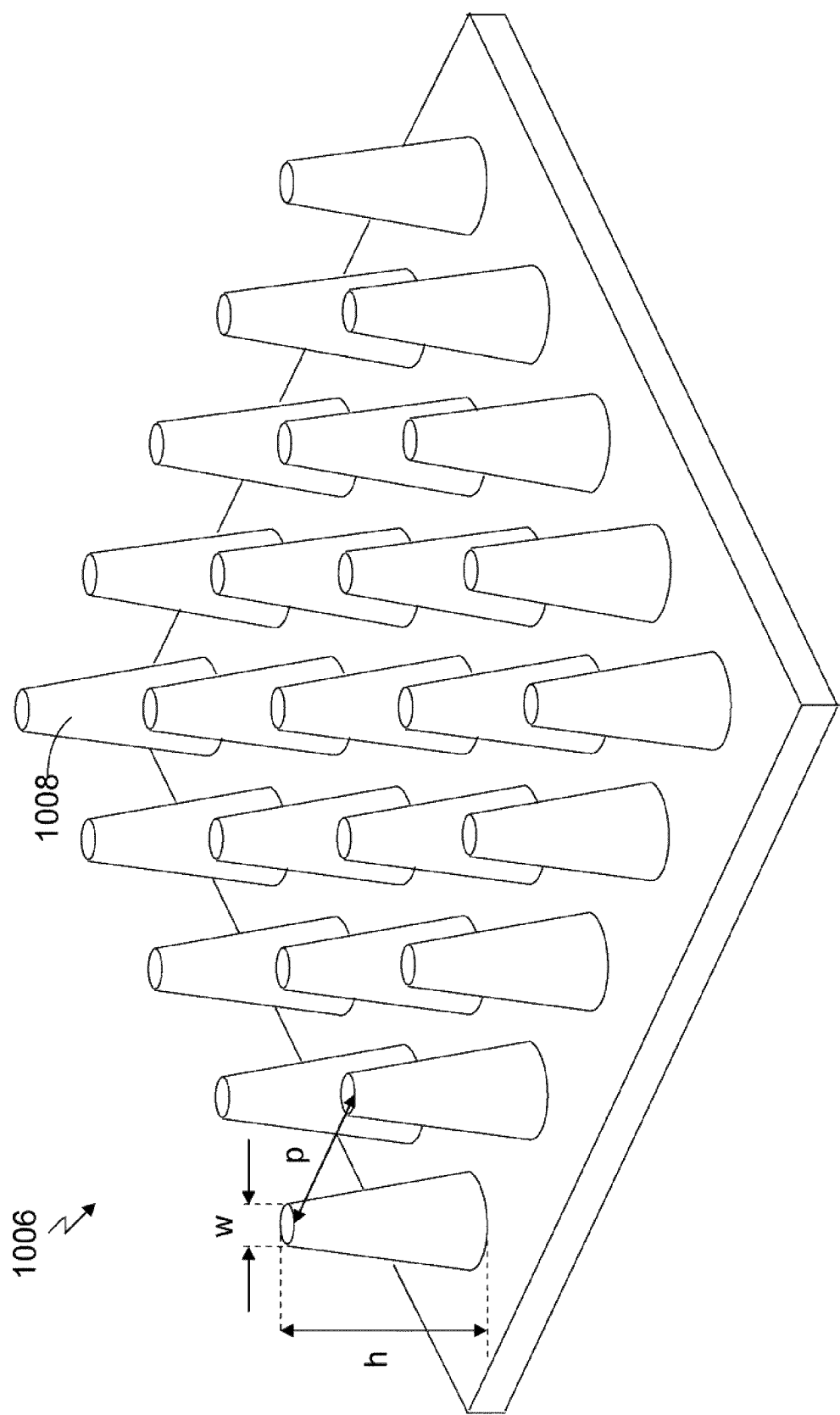
FIG. 10 illustrates an array of micro-columns according to an embodiment discussed herein.

In one embodiment, the micro-pattern on the polymer coating may include an array of pillars 1006, as shown in FIG. 10, arranged on arranged on all or a portion of the polymer coating surface. The pillars 1008 increase the adhesion of the polymer coating to the gum tissue by allowing the polymer coating to conform and adhere to the uneven surface of the tissue, thus maximizing interfacial contact to enhance adhesion. In the embodiment shown in FIG. 3, the pillars 1008 may be arranged in an area 332 of the polymer coating that is designed to be located within the gum line. This will allow the remaining gums to closely adhere to the polymer coating to facilitate gum growth along the remainder of the polymer coating.

The pillars 1008 may be prepared by patterning a silicon substrate using a combination of photolithography and reactive ion etching to generate a mold. The pillars 1008 may then be formed by molding and curing the polymer coating, for example using ultraviolet light or heat, as appropriate to the particular polymer. The dimensions of the pillars 1008, including the tip width w; height h, and pitch p, may vary. In one embodiment, the pillars 1008 may include tip widths w ranging from about 100 nm to about 1 μm and pillar heights h from about 0.8 μm to about 3 μm. The pillars 1008 may be coated with a layer of DXTA, to further improve their adhesion properties.

In other embodiments, the polymer coating may include, on a portion or all of the body, a micro-pattern sized to allow cells of the gums to grow directionally in one or two directions within the micro-pattern to promote rapid and efficient healing. For example, the dental implant 300 of FIG. 3 also includes a micro-pattern to promote directional cellular growth arranged on an area 334 that will protrude from the gum line into the area previously occupied by the papilla. The micro-pattern may include micro-features such as micro-tubes, troughs, and/or ridges arranged on the surface of the polymer coating in one, two, or more directions. The dimensions of the micro-features may be sized to allow the cells of the gums to grow within them. In various embodiments, the widths of the micro-features may be between about 0.5 μm to about 100 μm, larger than 100 μm, or between about 10 μm to about 40 μm.

The anchor of the dental implant may include various features to affix it firmly in a patient's jaw. As shown in FIG. 4, the anchor 420 extending from the base 414 of the body 410 of the dental implant 400 may include a screw 430 with a sharp terminal end 422 to allow it to be screwed into place in a patient's jaw. As shown in FIG. 5, the anchor 520 extending from the base 514 of the body 510 of the dental implant 500 may include a number of holes 530 to facilitate bone growth through the anchor 520.

Figure 6B:
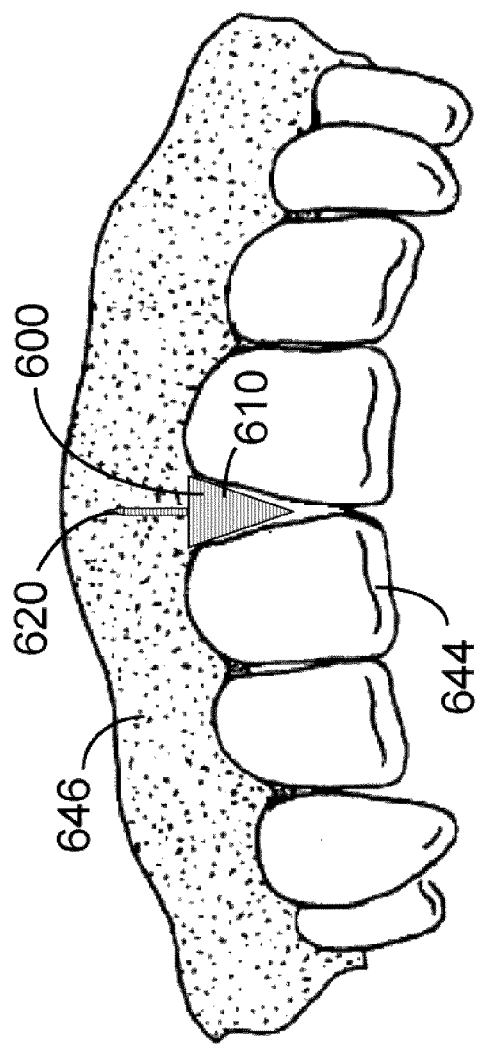
Figure 6C:
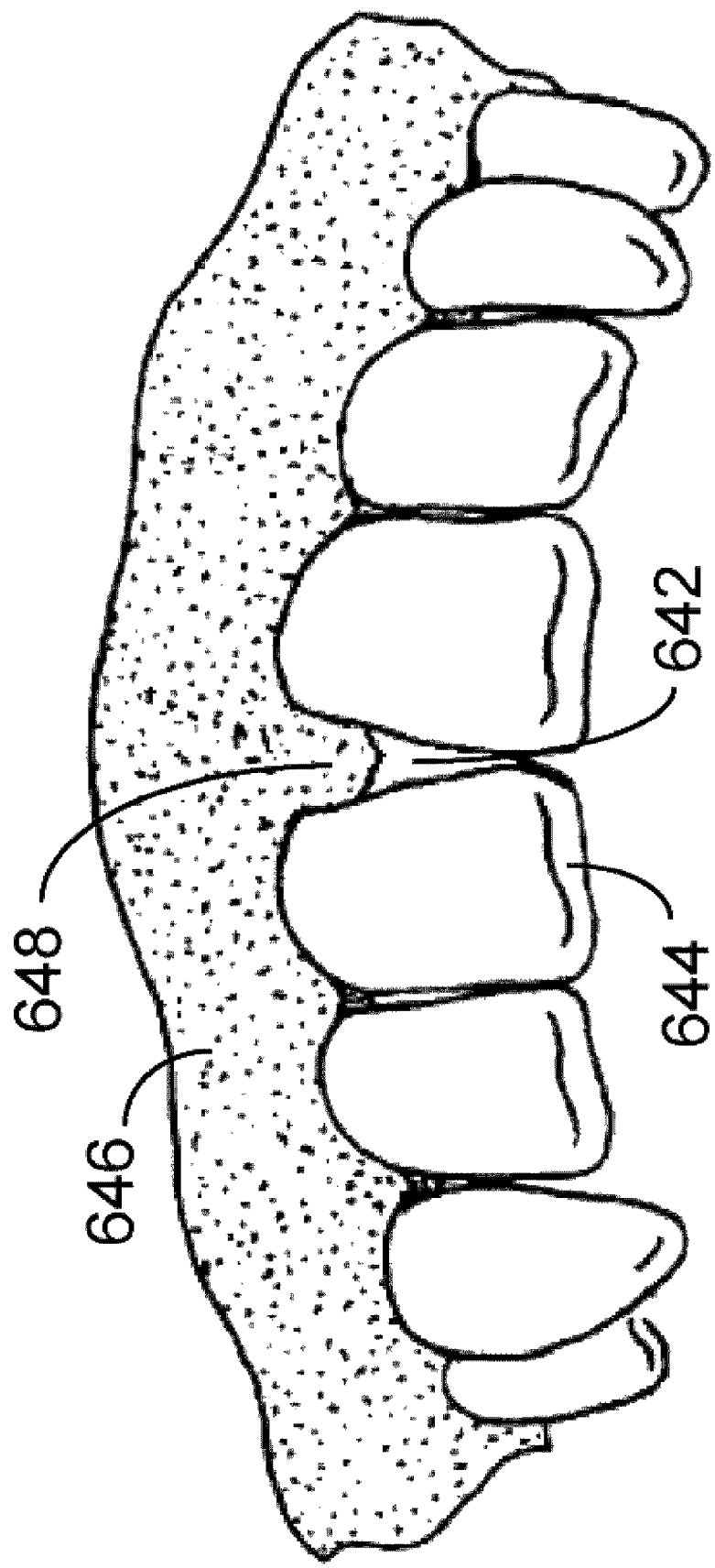

FIGS. 6A-6C shows stages of a method of implanting a dental implant in accordance with an embodiment. FIG. 6A shows the gums 646 and teeth 644 of a patient having a diastema 642 between the two front teeth. FIG. 6B shows a dental implant 600 in accordance with the various embodiments described above implanted into the gums 646 of the patient. The anchor 620 may be inserted into the bone of the patient to anchor the dental implant 600 and the body 610 may extend from within the gum line out into the diastema 642 to provide a substrate on which the gums may regrow. FIG. 6C shows the gums 646 after the dental implant 600 has been removed or has degraded. As shown in FIG. 6C, the papilla has regrown to partially fill the diastema 642. In other embodiments, the papilla may be regrown to fully fill the diastema 642.

As described above, one problem associated with the failure of a prosthesis is the inability of the surrounding bone to support the load of the implant. This is especially true in areas that are weaker due to the softer, porous, less dense, or spongier nature of the alveolar bone or jaw bone. In particular, dental implants are prone to fail due to lateral, anterior or posterior movement of the prosthesis together with lack of a rigid surrounding bone structure. This problem similarly affects the stabilization of a tooth implant or prosthesis.

Another problem with the failure of a prosthesis is due to a deteriorating jaw bone. When an extracted or otherwise missing tooth is not immediately grafted or replaced with an implant, atrophy of the jaw bone occurs over time resulting in compromise esthetics and compromised ability to function.

Embodiments discussed herein offer solutions to the foregoing problems by providing fillers that can be injected into a bone defect, conform to the shape of the defect, solidify to enhance the structural integrity of the bone, reduce bone deterioration, and protect the original (pre-extraction) shape of the bone itself. According to one embodiment, a filler comprises a viscous material that will solidify into a structured, matrix-like material. When injected, the filler typically has a viscosity that allows it to take on the shape of the jaw bone or skeletal deficiency to fit the dimensions of the cavity more or less exactly depending on the viscosity of the filler. The viscosity of the filler may be modified according to the intended use, from only a slightly malleable paste to a runny liquid. Optionally, surgery may be performed to "clean" the site (e.g., remove extra tissue and/or bone fragments, etc.) before applying the filler. After insertion, the site may be closed up using conventional sutures or an adhesive patch. An exemplary adhesive patch is described in U.S. Provisional Patent Application No. 61/238,019.

After the filler is solidified in the cavity of bone, natural infiltration occurs as a result of, and facilitated by, the filler such that new bone growth fills the internal cavity and replaces biodegradable portions of the filler. Alternatively, the bone growth may fill internal pores of the filler formed by the matrix nature of the filler. The material comprising the filler functions as an ideal growing environment for newly formed bone. By using the filler, new bone growth will occur (at an accelerated pace if seeded or grow at a normal pace if unseeded), as explained in greater detail below. The new bone growth can be used to support a prosthesis or denture with enhanced stability compared to a prosthesis or implant without such bone growth. Optionally, the resulting integrated bone structure of the filler can be cored or otherwise shaped to create an opening to accommodate an implant device.

The purpose of the filler is to preserve bone tissue and facilitate new bone growth such that jaw bone deterioration is prevented. Another purpose is to minimize the loss of bone volume. These goals are achieved by placing the filler into the defect, and creating an ideal growth environment to facilitate new bone growth and preserve the original contours of an individual's jaw bone tissue.

The filler is a degradable or non-degradable bioceramic material, e.g., hydroxyapatite, reinforced polyethylene composite, betatricalciumphosphate, substituted calcium phosphates, bioactive glass, resorbable calcium phosphate, alumina, zirconia, etc. in a viscous form that will solidify inside a bone cavity as a solid or mesh-like structure. It should also be noted that a biodegradable polymer can be used in combination with the bioceramic material to form a composite filler material. It should be appreciated that the filler may include any type of material known in the art having characteristics that result in non-toxic byproducts and that may solidify after application.

For example, the filler can be formed of synthetic polymers (alone or in combination) such as polyurethanes, polyorthoesters, polyvinyl alcohol, polyamides, polycarbonates, poly(ethylene)glycol, polylactic acid, polyglycolic acid, polycaprolactone, polyvinyl pyrrolidone, marine adhesive proteins, and cyanoacrylates, or analogs, mixtures, combinations, and derivatives of the above. The filler can also be formed of naturally occurring polymers or natively derived polymers (alone or in combination) such as agarose, alginate, fibrin, fibrinogen, fibronectin, collagen, gelatin, hyaluronic acid, and other suitable polymers and biopolymers, or analogs, mixtures, combinations, and derivatives of the above. Also, the filler can be formed from a mixture of naturally occurring biopolymers and synthetic polymers. Alternatively, the filler can be formed of a collagen gel, a polyvinyl alcohol sponge, a poly(D,L-lactide-co-glycolide) fiber matrix, a polyglactin fiber, a calcium alginate gel, a polyglycolic acid mesh, polyester (e.g., poly-(L-lactic acid) or a polyanhydride), a polysaccharide (e.g., alginate), polyphosphazene, or polyacrylate, or a polyethylene oxide-polypropylene glycol block copolymer. The filler can be produced from proteins (e.g. extracellular matrix proteins such as fibrin, collagen, and fibronectin), polymers (e.g., polyvinylpyrrolidone), or hyaluronic acid. Synthetic polymers can also be used, including bioerodible polymers (e.g., poly(lactide), poly(glycolic acid), poly(lactide-co-glycolide), poly(caprolactone), polycarbonates, polyamides, polyanhydrides, polyamino acids, poly-ortho esters, polyacetals, polycyanoacrylates), degradable polyurethanes, non-erodible polymers (e.g., polyacrylates, ethylene-vinyl acetate polymers and other acyl substituted cellulose acetates and derivatives thereof), non-erodible polyurethanes, polystyrenes, polyvinyl chloride, polyvinyl fluoride, poly(vinylimidazole), chlorosulphonated polyolifins, polyethylene oxide, polyvinyl alcohol, Teflon®, and nylon.

Bioceramics employed as the filler can fall into all three biomaterial classifications, i.e., inert, resorbable and active, meaning they can either remain unchanged, dissolve or actively take part in physiological processes. There are several calcium phosphate ceramics that are considered biocompatible and possible materials for the filler. Of these, most are resorbable and will dissolve when exposed to physiological environments, e.g., the extracellular matrix. Some of these materials include, in order of solubility: Tetracalcium Phosphate ($Ca_4P_2O_9$)>Amorphous calcium Phosphate>alpha-Tricalcium Phosphate ($Ca_3(PO_4)_2$)>beta-Tricalcium Phosphate ($Ca_3(PO_4)2$)>>Hydroxyapatite ($Ca_{10}(PO_4)_6(OH)_2$). Unlike the other certain calcium phosphates listed above, hydroxyapatite does not break down under physiological conditions. In fact, it is thermodynamically stable at physiological pH and actively takes part in bone bonding, forming strong chemical bonds with surrounding bone. This property is advantageous for rapid bone repair after surgery. Other bioceramic materials such as Alumina and Zirconia are known for their general chemical inertness and hardness. These properties can be exploited for implant device support purposes, where it is used as an articulating surface for implant devices. Porous alumina can also be used as a bone spacer, where sections of bone have had to be removed due to various conditions or diseases. The material acts as a scaffold or matrix for bone growth.

In one embodiment, the filler may have placed over it a reinforced polymer and/or composite coating that covers the filler. For example, when the filler includes a bioceramic material, the polymer coating may include a polyactic acid or other hydrogel, which may be arranged over the filler as further described below. It should be appreciated that polymer coating does not have to be a complete polymer material, e.g., 100% polymer, but can be a composite material comprising a combination of any known bioceramic materials, composite hydrogels, and polymers. Moreover, the polymer coating can be made from a membrane such as collagen felt, or a similarly semi-rigid material, such as polylatic acid, polyether, etc. In the preferred embodiment, polymer coating is a bio-resorbable polymer. The preferred bio-resorbable polymer exhibits characteristics such as favorable handling properties that make the polymer easy to use (i.e., requires no additional training for the operator to learn how to use, long-term, indefinite shelf life, economical, does not add considerable cost to patients, conforms to the receptor site, highly biocompatible and partially biodegradable, low cost to manufacturer, biomimetic after placement, easy to distribute, space maintenance (maintains shape of bone), supports cell growth and differentiation, chemotaxic properties (recruits wound healing host cells from surrounding tissue), and osteoconductive and osteoinductive). In addition, the polymer coating serves the purpose of preventing contamination of material while safe guarding, and not altering, the environment of an individual's mouth. The polymer may be infused within the filler as a liquid or viscous gel substance.

The filler can also include an additional bone morphogenic protein (BMP) material by incorporating the BMP into the filler. The additional protein serves as a stimulus for bone growth, in other words, an additional mechanism by which to promote accelerated bone growth within the filler. The BMPs induce new bone growth within the filler through a process resembling endochondral bone formation. In one embodiment, the BMP material comprises a protein substance and is mixed into the filler forming a composite filler material. The filler also can be infused with a collagen bone morphogenic protein base. It should be appreciated that the protein material may also comprise other growth proteins. Fibrinogen, α-thrombin, as well as other various antibiotics, growth hormones, gene therapies, or combinations of these factors may also be utilized in the filler to promote healthy bone growth. The BMP material may be infused within the filler as a liquid or viscous gel substance.

It should be noted that filler may include a material having a mesh-like structure. After solidifying, the filler may include a mesh-like structure that allows the new bone growth to grow throughout the filler. The mesh-like filler, in comparison to a solid structure, provides a greater amount of exposed surface area for bone growth to occur. The mesh-like filler has a porous nature and its pores can be substantially uniform or non-uniform to serve as a scaffold for the new bone growth. The pores can be formed in a variety of ways. In one embodiment, the filler may include micro-tubes mixed into the filler in its viscous state. When the filler solidifies, the micro-tubes provide a network of pores through which bone may grow. In another embodiment, the filler may include granules of a material that will degrade in the oral environment more quickly than the rest of the filler materials to form a number of pores through the solidified filler. In yet another embodiment, the filler may include granules of a material that will degrade upon contact with a fluid introduced into the patient's mouth, such as a mild and tolerable base or acid solution or an enzyme. In yet another embodiment, the filler may be formed of a material that naturally forms pores upon solidification.

At times, biodegradable polymers suffer from warping, hollowing or substantial erosion inherent with the process of degradation. In order to manage such a problem, polymers with high crystallinity are utilized. Self-reinforced and ultra-high strength bioabsorbable composites are readily assembled from partially crystalline bioabsorbable polymers, like polyglycolides, polylactides and glycolide/lactide copolymers. These materials have high initial strength, appropriate modulus and strength retention time from 4 weeks up to 1 year in-vivo, depending on the implant geometry. Reinforcing elements such as fibers of crystalline polymers, fibers of carbon in polymeric resins, and particulate fillers, e.g., hydroxyapatite, may also be used to improve the dimensional stability and mechanical properties of biodegradable filler. The use of interpenetrating networks (IPN) in biodegradable material construction has been demonstrated as a means to improve mechanical strength. To further improve the mechanical properties of IPN-reinforced biodegradable materials, biodegradable plates may be prepared as semi-interpenetrating networks (SIPN) of crosslinked polypropylene fumarate within a host matrix of poly(lactide-co-glycolide) 85:15 (PLGA) or poly(l-lactide-co-d,l-lactide) 70:30 (PLA) using different crosslinking agents.

Resin composites with incorporated polytetrafluoroethylene (PTFE) particles improve the hydrophobicity and surface properties of device implants, e.g., filler 700. PTFE has high resistance to chemical regents, low surface energy, tolerance to low and high temperatures, resistance to weathering, low friction wiring, electrical insulation, and slipperiness. However, because conventional PTFE has poor resistance to abrasion, the inventor contemplates cross-linking PTFE with gamma-beam irradiation can be employed to drastically enhances resistance to abrasion and deformation. Further, the composites made of braided carbon fibers and epoxy resins (so called biocompatible carbon-epoxy resin) have better mechanical properties than composites made of short or laminated unidirectional fibers.

Figure 7B:
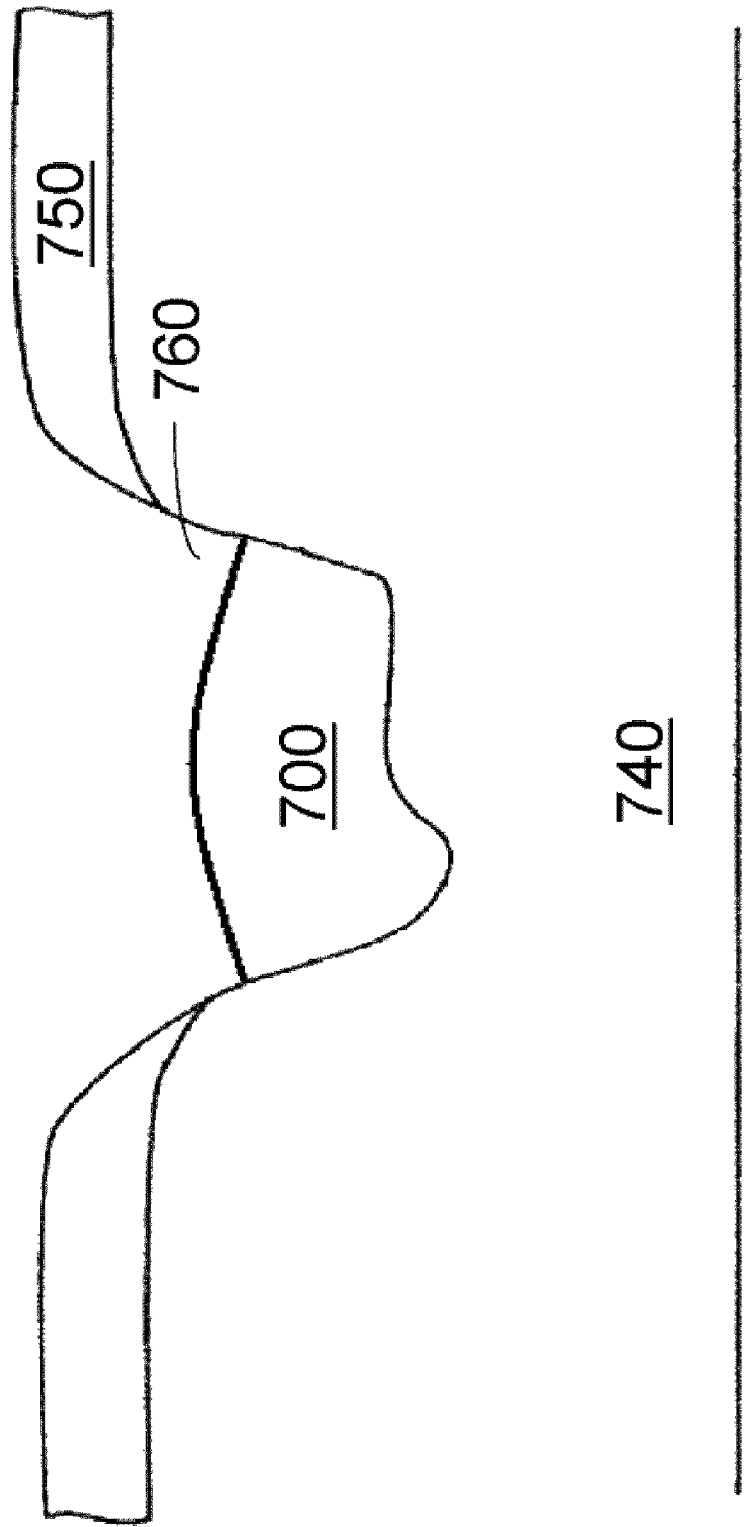
Figure 7C:
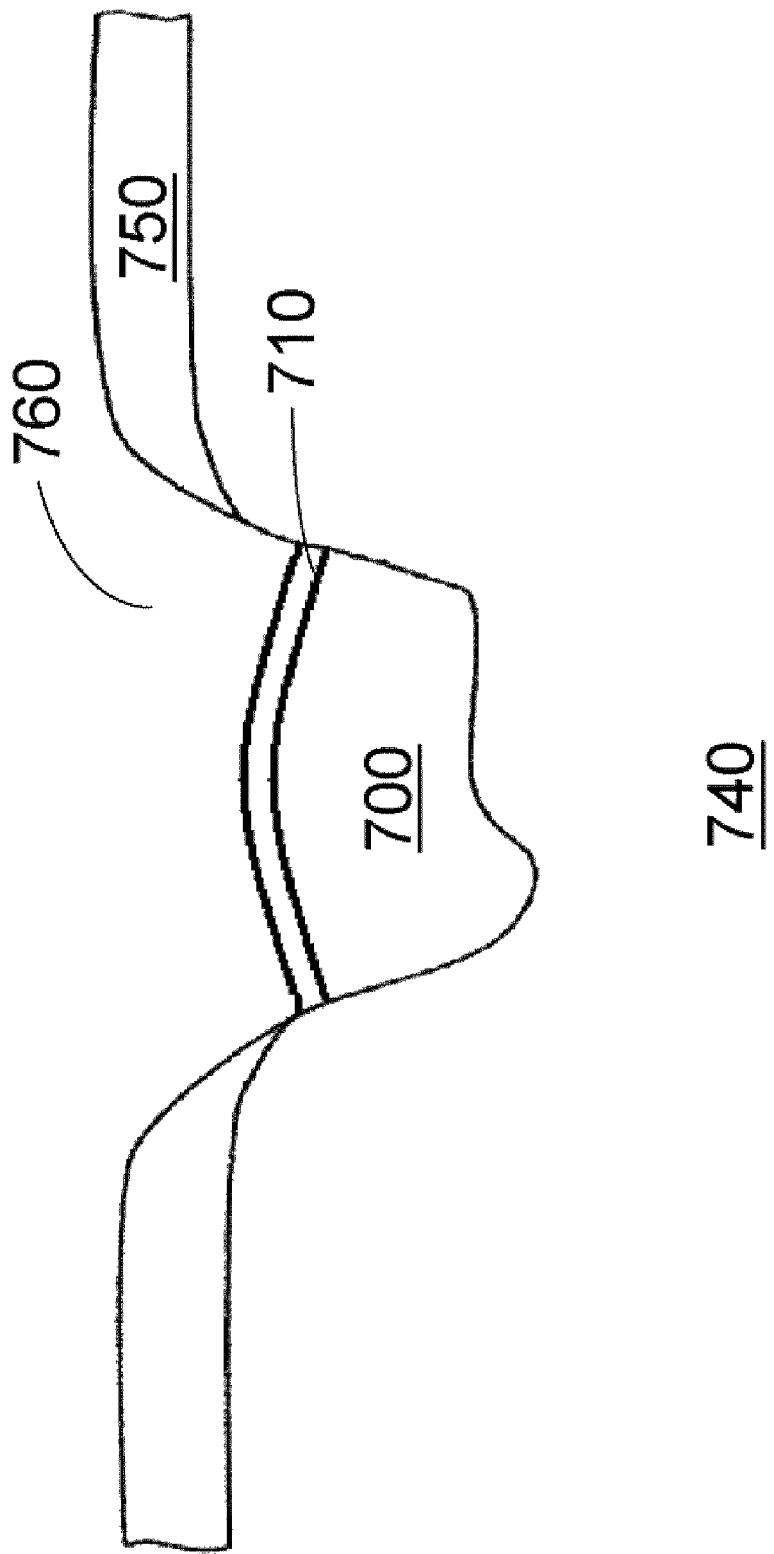

FIGS. 7A-7C show various stages of one particular application of the filler. By way of example, this sequence of drawings shows the implantation of a filler into a receptor site. FIG. 7A shows a cross-section of bone 740 having an opening or cavity 760 surrounded by an epithelial tissue layer 750. In the case of a dental implant, cavity 760 may represent the space created by avulsion of the natural tooth previously occupying that space prior to extraction. In other applications, the cavity 760 may be created by the removal of either damaged or healthy bone in order to provide an attachment site for the implant device. Cavity 760 can also be created by the removal of cancerous tissue or tissue affected by any other type of disease capable of affecting the strength or shape of the tissue. Prior to inserting the filler 700 into the cavity 760, the cavity 760 is cleaned and may be shaped utilizing conventional methods known in the art. As explained above, cavity 760 may be created by the removal of a natural tooth. In other instances, cavity 760 may result from the defect of a long bone created, for example, by debritement of a dysplasila. Cavity 760 can also result from any type of surgical procedure resulting in bone removal or any type of procedure that creates any type cavity.

FIG. 7B shows the cross-section of FIG. 7A following insertion of the filler 700 into cavity 760. The filler 700 has a viscosity allowing it to conform in part or completely to the size and shape of the bone cavity 760. In one embodiment, the filler 700 may have a viscosity allowing it to flow easily into and conform to the bone cavity 760. In another embodiment, the filler 700 may have a paste-like viscosity and may be physically pressed to conform to the bone cavity 760. Once placed into cavity 760, the filler 700 solidifies and remains secure seated within the cavity. In various embodiments, the cavity 760 may be shaped, or roughed up, to provide adequate ridges or crags with which the tiller may interlock.

As shown in FIG. 7C, an optional polymer coating 710 may be applied over the filler 700. The polymer coating 710 may be applied as a viscous material that conforms to an then solidifies over the filler 700. In various embodiments, the polymer coating 710 may be applied to the filler 700 before or after the filler 700 itself has solidified. The polymer coating 710 interacts with the blood surrounding cavity 760 to form a securing mechanism, e.g., a blood clot, that further secures the filler 700 in place. The barrier layer formed by the polymer coating 710 prevents mucosal attachment or soft tissue growth which would inhibit bone growth. Instead, osteointegration of new bone growth to and within the filler 700 is permitted to occur.

Figure 8:
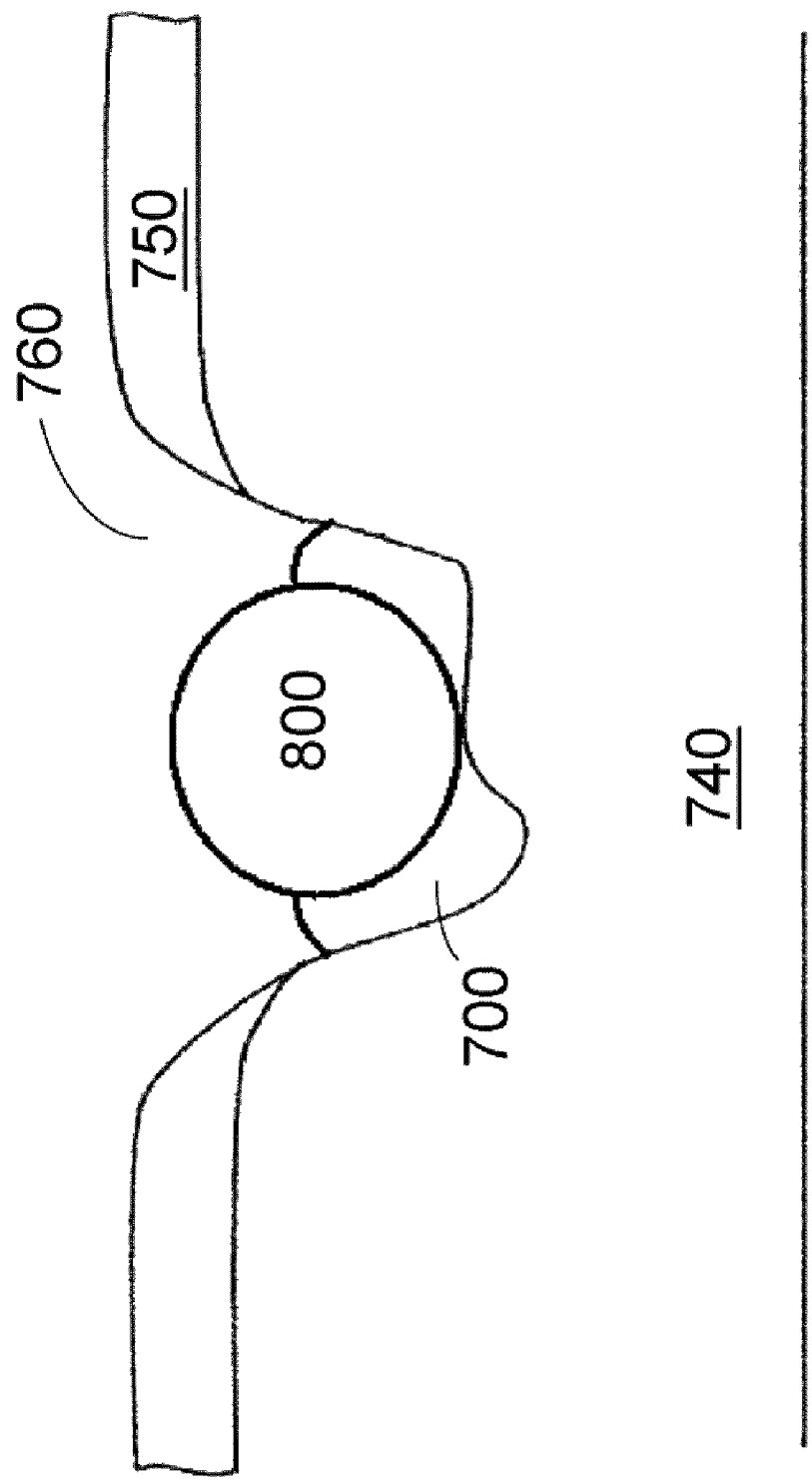
FIG. 8 illustrates a method of performing bone augmentation in accordance with another embodiment discussed herein.

As shown in FIG. 8, the filler 700 may be used in combination with a solid pellet 800 for facilitating bone growth, for example, the pellets described in U.S. patent application Ser. No. 12/350,754, the disclosure of which is incorporated herein by reference in its entirety. The pellet 800 may be inserted into bone cavity 760 and the filler 700 may be used to fill in the areas around the pellet 800 to cause the pellet 800 to be securely affixed in the cavity. The pellet 800 and the filler 700 may comprise the same or different materials. In one embodiment, the pellet 800 may include a number of cavities into which the filler 700 may infiltrate to interlock the pellet 800 and the filler 700 once the filler 700 solidifies. In various embodiments, the filler 700 may cover part or all of the pellet 800.

Figure 9:
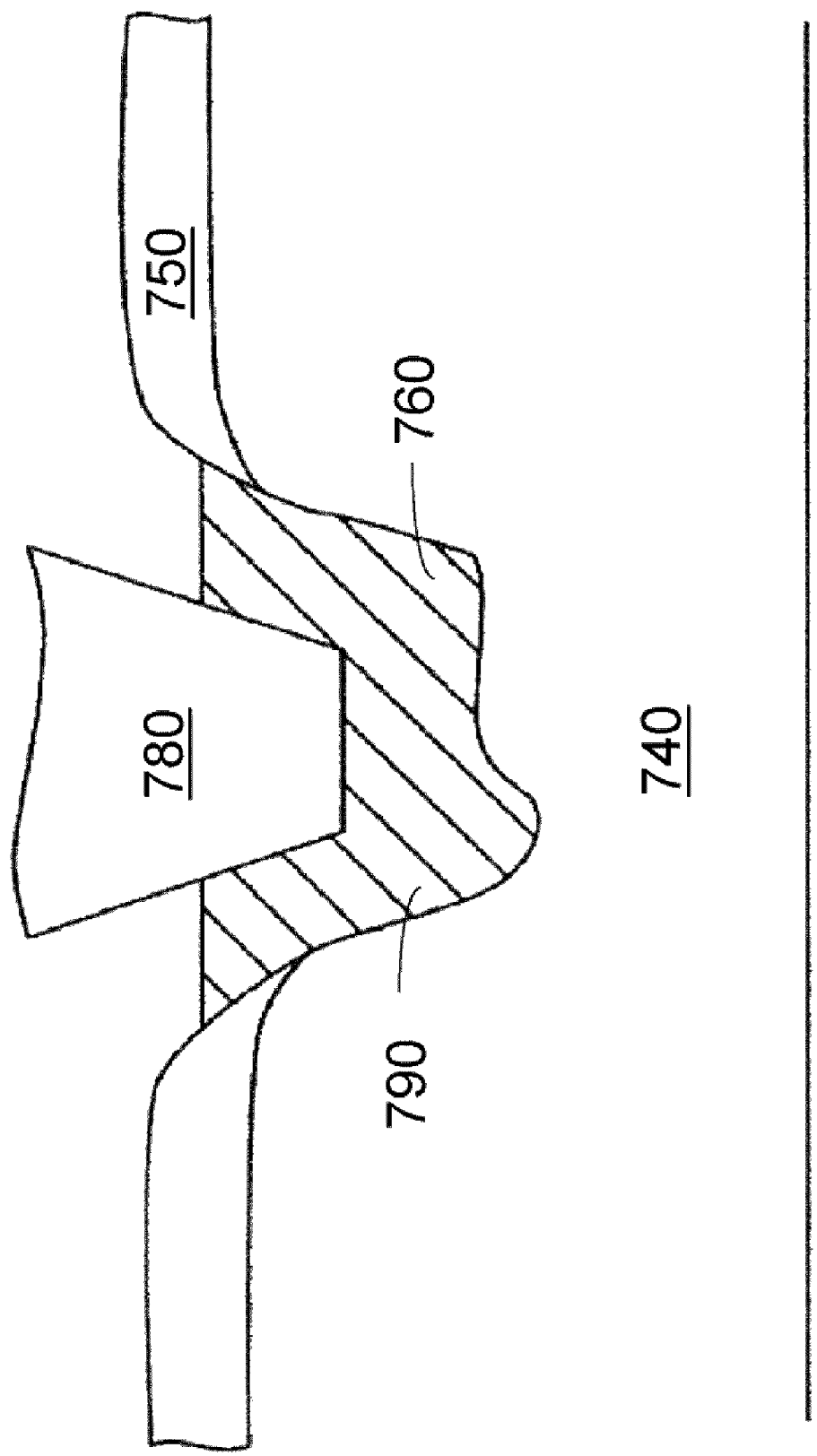
FIG. 9 illustrates another method of performing bone augmentation in accordance with another embodiment discussed herein.

Once bone growth into the cavity 760 is complete, the region can be used to support a prosthesis or may be cored or otherwise shaped to accept an implant device. FIG. 9 illustrates a bottom portion of an implant device 780 fixably secured/attached to bone 740 using the newly grown osteointegration bone 790. The osteointegrated bone 790, consisting of new bone, provides improved fixation for implant 780 over the previously existing deteriorated bone. Over time, it is expected that the bone 790 will further integrate onto the outer, submerged surface layer of implant 780.

It should be appreciated that additional applications exist for use in long bone or exo-augmentation. For example, this may involve the augmentation of bone onto the surface of existing skeletal bone. It is appreciated that the various embodiments described herein are also useful in the treatment of a fractured or shattered bone. The filler allows for bone integration at the damaged site as well as soft-tissue attachment to the surrounding soft tissue. It is appreciated that various amounts of the filler may be used to form a variety of sizes. That is, due to its viscous nature, it may be molded or adapted to fit a particular application or circumstance.

What is claimed as new and desired to be protected by Letters Patent of the United States is:

1. A method of performing bone augmentation, said method comprising:
   arranging a pellet in a bone cavity;
   arranging a first material around the pellet in the bone cavity, wherein the first material comprises a viscosity that allows it to conform to a shape of the bone cavity;
   arranging a second material in the bone cavity as a layer on top of the first material, wherein the second material comprises a viscosity that allows it to conform to a shape of the first material;
   solidifying the first material; and
   solidifying the second material.

2. The method of claim 1, wherein said solidified first material comprises a bioceramic material.

3. The method of claim 1, wherein said solidified second material comprises a bio-resorbable polymer.

4. The method of claim 1, further comprising coring an osteointegrated bone structure formed by the solidified first and second materials to form a bone void; and inserting an implant device into said bone void.

5. The method of claim 1, wherein when said first material and said second material are arranged in an edentulous ridge.

6. The method of claim 1, wherein the first material is solidified before the second material is arranged on top of the first material.

7. The method of claim 1, wherein the solidified first material comprises a plurality of pores formed by a plurality of micro-tubes.

8. The method of claim 1, wherein the first material comprises granules of a third material, and wherein the method further comprises degrading the granules of the third material using a fluid to form a plurality of pores in the first material after solidifying the first material.

9. The method of claim 8, wherein the fluid comprises one of an acid, a base, and an enzyme.

10. The method of claim 1, wherein the first material naturally forms pores upon solidification.

11. The method of claim 1, further comprising removing a tooth to form the bone cavity.

* * * * *